(12) United States Patent
Hidaka et al.

(10) Patent No.: US 7,297,821 B2
(45) Date of Patent: Nov. 20, 2007

(54) FLUORINE COMPOUND AND FLUORINATING AGENT COMPRISING THE COMPOUND

(75) Inventors: Toshio Hidaka, Ibaraki (JP); Norio Fushimi, Ibaraki (JP); Takafumi Yoshimura, Ibaraki (JP); Takeshi Kawai, Ibaraki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/297,408

(22) Filed: Dec. 9, 2005

(65) Prior Publication Data

US 2006/0089513 A1    Apr. 27, 2006

Related U.S. Application Data

(62) Division of application No. 10/433,412, filed as application No. PCT/JP02/08477 on Aug. 22, 2002, now Pat. No. 7,019,173.

(30) Foreign Application Priority Data

Aug. 28, 2001 (JP) .............................. 2001-257833

(51) Int. Cl.
    *C07C 211/00* (2006.01)
(52) U.S. Cl. ..................... 564/384; 568/17; 570/123
(58) Field of Classification Search ............... 564/384; 568/17; 570/123
    See application file for complete search history.

(56) References Cited

U.S. PATENT DOCUMENTS

| 2,859,245 A |   | 11/1958 | Smith |
| 2,879,302 A |   | 3/1959  | England et al. |
| 3,092,637 A | * | 6/1963  | Brown ........................ 548/574 |
| 3,882,182 A |   | 5/1975  | Benninger et al. |
| 4,353,830 A | * | 10/1982 | Mark ........................... 548/558 |
| 4,788,339 A |   | 11/1988 | Moore et al. |
| 5,874,616 A |   | 2/1999  | Howells et al. |
| 5,925,611 A |   | 7/1999  | Flynn et al. |
| 5,962,390 A |   | 10/1999 | Flynn et al. |
| 5,977,237 A |   | 11/1999 | Shin et al. |

OTHER PUBLICATIONS

Dmowski et al., Reactions of N,N-dialkylbenzamides with sulfur tetrafluoride. Formation of dialkyl-a,a difluorobenzylamines, Polish Journal of Chemistry (1982), 56(10-12), 1369-78.*

Dmowski et al., {Reactions of N,N-dialkylbenzamides with sulfur tetrafluoride. Formation of dialkyl-a,a difluorobenzylamines, Polish Journal of Chemistry (1982), 56(10-12, 1369-78}.*

Supplementary European Search Report, for Application No. EP 02 76 0710, dated Dec. 20, 2005.

D. J. Brauer, et al., "Synthesis, Vibrational Spectra, and Crystal Structure Analysis of Di- and Trifluoro-tetra-methylammonium Salts", Z. anorg. Allg. Chem., vol. 537, pp. 63-78, 1986.

I. L. Knunyants, et al., "Alpha-Fluoroalkylamines, a new source of unhydrated fluoride ion", Bulletin of the Academy of Sciences of the USSR. Division of Chemical Science, Consultants Bureau, vol. 30, No. 4, pp. 639-642, Oct. 10, 1981.

F. S. Fawcett, et al., "The Chemistry of Carbonyl Fluoride. I. The Fluorination of Organic Compounds", *Journal of the American Chemical Society*, vol. 84, No. 22, pp. 4275-4285, Nov. 20, 1962.

A. Colens, et al., "Reactivity and Synthetic Potential of Alpha-Fluoro- and Alpha-Iodoenamines", *New Journal of Chemistry* (France), vol. 1, No. 5, pp. 371-372, 1977.

Z. Arnold, "Synthetic Reactions of Dimethylformamide. XIX. Preparation of Alpha, Alpha- Difluorotrimethylamine and Some of its Reactions", Collection of Czechoslovak Chemical Communications, Institute of Organic Chemistry & Biochemistry, Prague, CZ, vol. 28, No. 8, pp. 2047-2051, 1963.

(Continued)

*Primary Examiner*—Yvonne (Bonnie) Eyler
*Assistant Examiner*—Chukwuma Nwaonicha
(74) *Attorney, Agent, or Firm*—Antonelli, Terry, Stout & Kraus, LLP.

(57) ABSTRACT

A fluorine compound represented by Formula (1) is provided. The above fluorine compound is effective for introducing a fluorine atom into a compound having an active group such as an oxygen-containing functional group, and it can be used for uses of surface treatment, cleaning and coating. Further, after the fluorination reaction, the above compound is recovered and can be reused as a starting material for producing the above fluorine compound, and it is useful for various fluorination processes.

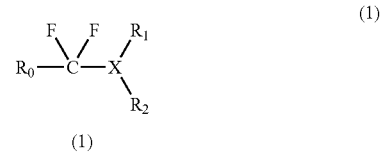

(1)

(wherein X represents a nitrogen or phosphorus atom; $R_0$, $R_1$, and $R_2$ represent hydrogen, an alkyl group or aryl group which may have a substituent, and they each may be the same or different; and $R_0$, $R_1$, and $R_2$ may be combined with each other to form a ring).

1 Claim, No Drawings

OTHER PUBLICATIONS

G. W. Parshall, et al., "Addition of Phosphines to Fluoroölefins", *Journal of the American Chemical Society*, vol. 81, No. 18, pp. 4801-4802, Sep. 20, 1959.

E. C. Wang, et al., "Microwave Spectrum, Electric Dipole Moment and Barriers to Internal Rotation of Trans and Gauche-Difluoromethylphosphine $CHF_2PH_2$", *Journal of Molecular Structure*, vol. 223, pp. 15-32, 1990.

J. Dyer, et al., "Nuclear Magnetic Resonance Spectra of Fluorinated Alkylphosphines", *Journal of the Chemical Society*, Section B: Physical Organic Chemistry, pp. 409-412, 1970.

W. Dmowski, et al., "Reactions of N,N-dialkylbenzamides with sulfur tetrafluoride", *Pol. J. Chem.*, vol. 56, Nos. 10-12, pp. 1369-1378, 1982.

W. Dmowski, et al., "Dialkyl-α, α-difluorobenzylamines and dialkyl (frifluoromethyl) amines", *J. Fluorine Chem.*, vol. 23, No. 3, pp. 219-228, 1983.

C. Belzecki, et al., "Asymmetric synthesis of β-lactams", *J. Chem. Soc.*, Chem. Commun., No. 2, pp. 57-58, 1981.

G. Bissky, et al., "Generation of Heteroarylium-N-Difluoromethylides and Heteroarly-N-Difluoromethyl Anions and their Reaction with Electrophiles: Heteroaryl- and Heteroarylium-N-Difluoromethyl Trimethylsilanes and a New Heteroaryl-N-Difluoromethane", *Journal of Fluorine Chemistry*, vol. 109, pp. 173-181, 2001.

G. W. Parshall, et al., "Addition of Phosphines to Fluoroölefins", *Journal of American Chemical Society*, vol. 81, pp. 4801-4802, 1959.

M. Grdinic, et al., "Chemistry of Imidoyl and Amide Chloride II. On the Preparation and Properties of the N- Mono- and N,N-Dialkyl-Substituted Amide Halides", *Journal of Organic Chemistry*, vol. 30, No. 7, pp. 2381-2384, 1965.

\* cited by examiner

FLUORINE COMPOUND AND FLUORINATING AGENT COMPRISING THE COMPOUND

This application is a Divisional application of application Ser. No. 10/433,412, filed Jun. 4, 2003, the contents of which are incorporated herein by reference in their entirety. Ser. No. 10/433,412 is a National Stage application filed under 35 USC 371, of International (PCT) Application No. PCT/JP02/08477, filed Aug. 22, 2002.

BACKGROUND OF THE INVENTION

The present invention relates to a fluorine-containing nitrogen group compound, particularly a fluorine-containing nitrogen compound. The fluorine-containing nitrogen group compound is useful for fluorination of compounds having active functional groups such as oxygen-containing compounds and surface treatment, coating and cleaning uses of various materials.

RELATED ART

A large part of fluorine-containing compounds shows a specific biological activity and an excellent function which originate in a fluorine atom. In recent years, usefulness of introducing fluorine is recognized particularly in the fields of medicines and agricultural chemicals, and fluorine-containing compounds are increasingly required. Further, they are applied making the best use of functions thereof not only in the fields of medicines and agricultural chemicals but also in the wide fields, and the importance of fluorine-containing compounds grows high further more.

Fluorine-containing compounds are scarcely present in the natural world, and therefore fluorine atoms have to be introduced in an organic synthetic manner. For example, fluorine, hydrogen fluoride and sulfur tetrafluoride are known as a conventional fluorinating agent used for the purpose of introducing fluorine. However, they are toxic and corrosive and have the risk of explosion in the reaction, and therefore they have the problem that a specific apparatus and technique are required in handling. Further, they have the defect that they are low in a yield in the reaction and inferior in a selectivity in many cases.

In addition to them, various fluorinating agents have been developed in order to selectively introduce fluorine into oxygen-containing functional groups. Given as representative fluorinating agents are, for example, hydrogen fluoride-pyridine mixtures (Olah reagent), a Yarovenko reagent of a fluoroalkylamine type and an Ishikawa reagent which is a modified type thereof and diethylaminosulfur trifluoride which is known usually as DAST. However, all of them hold the problems of safety, storage stability and waste disposal after reaction, and the existing situation is that they are not necessarily satisfactory from an industrial point of view considering complexity in handling and the production.

DISCLOSURE OF THE INVENTION

An object of the present invention is to provide a compound which makes it possible to fluorinate functional groups such as an oxygen-containing group, which is excellent in heat stability and can easily be handled and which can be produced at a low cost.

Intensive investigations carried out by the present inventors in order to solve the problems described above have resulted in finding that a fluorine compound represented by Formula (1):

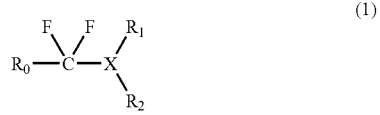

(wherein X represents a nitrogen or phosphorus atom; $R_0$, $R_1$, and $R_2$ represent hydrogen, an alkyl group or aryl group which may have a substituent, and they each may be the same or different; and $R_0$, $R_1$, and $R_2$ may be combined with each other to form a ring) is effective for fluorinating various oxygen-containing compounds, can be distilled, has a high heat stability, is easy in handling and therefore can solve a large part of the problems described above and that the above compound is useful as well for uses such as surface treatment and cleaning. Thus, they have reached the present invention.

Further, the present inventors have found that the compound represented by Formula (1) can be obtained by introducing fluorine atoms directly into a compound represented by Formula (2):

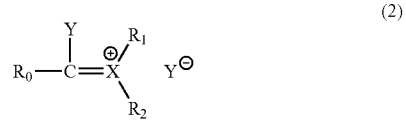

(wherein X represents a nitrogen or phosphorus atom; $R_0$, $R_1$, and $R_2$ represent hydrogen, an alkyl group or aryl group which may have a substituent, and they each may be the same or different; $R_0$, $R_1$, and $R_2$ may be combined with each other to form a ring; and Y represents chlorine, bromine or iodine) using a fluorinating agent or subjecting it to halogenation reaction with a halogenating agent.

BEST MODE FOR CARRYING OUT THE INVENTION

The fluorine compound represented by Formula (1) in the present invention is, to be specific, a fluorine-containing nitrogen group compound and includes a fluorine-containing nitrogen compound in which X is nitrogen in Formula (1) and a fluorine-containing phosphorus compound in which X is phosphorus in Formula (1).

The alkyl group represented by $R_0$, $R_1$, and $R_2$ is preferably a linear or branched alkyl group having 1 to 30 carbon atoms and includes, for example, methyl, ethyl, propyl, isopropyl, butyl, isobutyl, t-butyl, pentyl, hexyl, heptyl, octyl, 2-ethylhexyl, nonyl, decyl, cyclohexyl, cyclohexyloxy, decalyl, norbornyl, bicyclohexyl, adamantyl and isomers thereof, and in addition thereto, it includes hydroxymethyl, hydroxyethyl, hydroxypropyl, hydroxybutyl and hydroxyphenyl.

A group having 1 to 30 carbon atoms is preferred as the aryl group and includes, for example, phenyl, o-tolyl, m-tolyl, p-tolyl, dimethylphenyl and position isomers thereof, cumyl, mesityl, trimethylphenyl, hydroxyphenyl, naphthyl, methylnaphthyl, dimethylnaphthyl, hydroxynaphthyl, biphenyl, tetralyl, t-phenyl, anthryl, benzothienyl, chromenyl and indoyl. Allowed to be contained in these alkyl groups and aryl groups are other functional groups, for example, a hydroxyl group, a halogen group, a nitro group, a mercapto group, an amino group, amide group, a cyano group, a carbonyl group, a carboxyl group, an acetyl group, an acyl group, an alkoxy group, a sulfone group and other atomic groups.

The fluorine compound represented by Formula (1) can be produced by various processes. For example, the fluorine-containing nitrogen compound can usually be produced by a method in which an N,N-disubstituted amide compound which is an amide compound corresponding to the compound represented by Formula (1) is used as a starting material to directly introduce a fluorine atom using various fluorinating agents or a method in which fluorination reaction is carried out with a fluorinating agent and in which halogen exchange reaction is then carried out subsequently thereto to introduce fluorine.

The fluorine-containing phosphorus compound can readily be produced, for example, by a method in which a hydroxymethylphosphnium salt is obtained from phosphine and aldehyde and then reacted with amines.

The fluorine-containing nitrogen group compounds described above may be used considering physical and chemical characteristics, that is, heat stability, reactivity, easiness in handling and a price, but the fluorine-containing nitrogen compounds are more preferred from the viewpoints of a price and handling.

In producing the fluorine-containing nitrogen compound directly from the N,N-disubstituted amide compound, an oxygen-containing functional group can be fluorinated using fluorine, sulfur tetrafluoride, iodine pentafluoride, HF-bases and iodine pentafluoride-HF molten salts.

The fluorine-containing nitrogen compound is directly synthesized preferably using HF-bases such as HF-triethylamine and iodine pentafluoride-HF molten salts taking the reactivity and the safety into consideration.

One example of a process for producing the fluorine-containing nitrogen compound by halogen exchange shall be shown below.

(1) An N,N-disubstituted amide compound is reacted with a halogenating agent to produce a halide of the amide compound (hereinafter referred to as a step 1).

(2) Then, the halide of the amide compound described above is reacted with hydrogen fluoride or an alkaline metal salt of fluorine to carry out a halogen exchange reaction to thereby produce a fluorine-containing nitrogen compound (hereinafter referred to as a step 2).

In the production of the fluorine-containing nitrogen compound described above, a chlorinating agent such as phosgene, phosphorus trichloride, phosphorus pentachloride, thionyl chloride and oxalyl chloride are suitably used for halogenation in the step 1. An oxygen atom in the amide bond is substituted with halogen by virtue of these halogenating agents.

When a chlorine atom of the chlorinating agent has a low reactivity, a halogenating agent having a higher reactivity is preferably selected from similar halogenating agents containing bromine and iodine to introduce bromine or iodine. Usually, halogenation of acid amides readily goes on.

In the case of, for example, isobutyramide, the reaction is completed by allowing phosgene to flow at 20° C. in dichloromethane to carry out chlorination (Organic Synthesis, CV 6, 282).

The halogenating means described above provides a halide of an amide compound represented by Formula (3) which is a precursor of the compound represented by Formula (1):

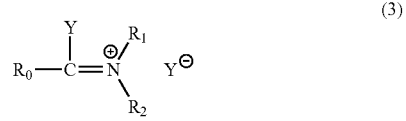

(wherein $R_0$, $R_1$, and $R_2$ represent hydrogen, an alkyl group or aryl group which may have a substituent, and they each may be the same or different; $R_0$, $R_1$, and $R_2$ may be combined with each other to form a ring; and Y represents chlorine, bromine or iodine).

In the production of the fluorine-containing nitrogen compound described above, it is difficult to definitely prescribe the conditions of a halogen exchange reaction carried out by a conventionally known process using hydrogen fluoride and an alkaline metal salt of fluorine such as sodium fluoride and potassium fluoride in the step 2, but almost all of the individual reactions are well known, so that the conditions can be decided with reference to publicly known literatures, for example, Journal of Organic Chemistry, vol. 44, p. 3872 (1979), Organic Synthetic Chemistry Society Magazine, vol. 47, p. 258 (1989) and Journal of Fluorine Chemistry, vol. 44, p. 291 (1989).

Preferred as the starting material is an N,N-disubstituted amide compound having an alkyl group or aryl group which may have a substituent.

The substituents may be the same as or different from each other and may be combined with each other to form a ring. Further, the substituents may have the other functional groups, for example, a hydroxyl group, halogen, a mercapto group, an amino group, an amide group, a carboxyl group, an acetyl group, a sulfone group and atomic groups thereof or may have similar alkyl groups and aryl groups.

To be specific, capable of being given are N,N-dimethylformamide, N,N-diethylformamide, N,N-di(n-propyl)formamide, N,N-di(i-propyl)formamide, N,N-di(n-butyl)formamide, N,N-dipentylformamide, N,N-dimethylacetamide, N,N-diethylacetamide, N,N-dimethylpropionamide, N,N-dimethyltrifluoroacetamide, N,N-dimethylcyanoformamide, N,N-dimethylcyclopropanecarboxyamide, N,N-dimethyl-2-thiooxamide, N,N-dimethylbenzeneacetamide, N,N-dimethylacetoacetamide, N,N-dimethyl-2,2-dichloroacetoacetamide, N,N-dimethylphenoxyacetamide, N,N-diethylpropionamide, N,N-diethylbutylamide, N,N-dimethylamide, N,N-dipropylacetamide, N,N-bis(2-hydroxymethyl)dodecaneamide, N,N-dimethylaminoethylmethacrylamide, N,N-diethyl-2-(1-naphthyloxy)propaneamide, N,N-dibutylacetamide, 1-triphenylphosphoranilidene-2-propane, N,N-diethyldecalylamide, N-methylformamide, N-methylacetamide, N,N-dimethylphenoxyacetamide, N-methyl-N-phenylformamide, N,N-dimethylbutyramide, N,N-dimethylisobutyramide, N,N-diethylisobutyramide, N,N-dimethylvaleramide, N,N-dimethylbenzamide, N,N-diethylmetatoluamide, N,N-diethyl-o-tolylamide, N,N-diethyl-p-tolylamide, N,N-diethyl(2,4-dimethyl)benzamide, N,N-diethyl(2,6-dimethyl)benzamide, N,N-dimethylaminoethylmethacrylamide, N,N-dimethylcinnamamide, N,N-dimethyl-furan-2-carboxyamide, N,N-dimethyl-furan-3-carboxyamide, N,N-dimethyl-p-chlorobenzamide, N,N-dimethyl-p-bromobenzamide, N,N-dimethyl-p-fluorobenzamide, N,N-diethylmesitylamide, N,N-diethylnaphthylamide, N,N-diethylbiphenylamide, N,N-diethylanthrylamide, N,N-diethylcyclohexylamide, N,N- dimethyldecaneamide, N,N-dimethylfuran-2-pyridine carboxyamide, benzoylpiperidine, and benzoylmorpholine. To be natural, the present invention shall not be restricted only to these examples given.

The fluorine-containing nitrogen group compound of the present invention obtained by the production process described above, particularly the fluorine-containing nitrogen compound can suitably be used as it is for fluorination of a compound having an active group which is reacted with a fluorine atom. An oxygen-containing functional group such as a hydroxyl group, a formyl group and a carboxyl group can be given as the active group which is reacted with a fluorine atom, and particularly, it is suited for fluorination of primary alcohol. It may be used together with an inactive solvent and diluent.

The fluorine-containing nitrogen compound of the present invention can be recovered in the form of an amide compound which is a raw material for the fluorine-containing nitrogen compound after finishing the reaction with an oxygen-containing group, and therefore a fluorination process in which recycle is possible can be set.

The fluorine-containing nitrogen compound can suitably be used for various fluorination processes such as not only an oxygen-containing compound and surface treatment of a material having an active functional group which is reacted with a fluorine atom but also coating and cleaning uses of a material surface.

Next, the present invention shall be explained in further details with reference to examples, but the present invention shall by no means be restricted by these examples.

The compounds in the examples were, analyzed by the following methods.

(1) Fluorine Content

A sample was completely burned by means of an oxygen-hydrogen combustion apparatus to absorb the whole amount of fluorine in water, and the absorbed solution was determined by means of a fluorine ion electrode.

(2) NMR Measurement

NMR-LA500SS (500 MHz) manufactured by Nippon Electron Co., Ltd. was used to carry out measurement in a deuterochloroform solvent.

EXAMPLE 1

Synthesis of N,N-diethyl-α-chlorometatoluylamidium chloride

A three neck flask (300 ml) was charged with a carbon tetrachloride (125 g) solution containing oxalyl chloride (25 g, 0.197 mol) under nitrogen atmosphere. N,N-diethylmetatoluamide (45 g, 0.236 mol, hereinafter abbreviated as DEET) was dropwise added thereto in 20 minutes while cooling the flask on ice and water and stirring. After finishing dropwise adding, the flask was maintained at the same temperature for 10 minutes to control the temperature of the content to 50° C., and then the reaction was continued for one hour. Gas was observed to be generated in the reaction, and then a white deposit was obtained. The resulting deposit was separated by filtering, washed with carbon tetrachloride and n-hexane and then dried to obtain N,N-diethyl-α-chlorometatoluylamidium chloride. N,N-diethyl-α-chlorometatoluylamidium chloride thus obtained was slowly heated up to 200° C. in a capillary tube (sealed tube). Decomposition was not observed, and it was thermally stable. It was found from thermal analysis carried out by TG-DTA that the melting point was 54.6° C.

NMR data:
$^1$H-NMR: δ value (ppm), TMS standard, measured in $CDCl_3$ 1.5 (t, $-CH_3$), 1.7 (t, $-CH_3$), 2.4 (s, $-CH_3$), 4.4 (q, $-CH_2-$), 4.5 (q, $-CH_2-$) 7.4 to 7.8 (aromatic ring hydrogen).

$^{13}$C-NMR: δ value (ppm), TMS standard, measured in $CDCl_3$ 12.5 (s, $-CH_3$), 13.6 (s, $-CH_3$), 21.3 (s, $-CH_3$), 54.8 (s, $-CH_2-$), 56.0 (s, $-CH_2-$), 125.1, 128.2, 129.5, 131.1, 135.1, 140.0 (s, aromatic ring $-CH-$×6), 174.1 (s, $-CCl$).

EXAMPLE 2

Synthesis of N,N-diethyl-α, α-difluoro(3-methyl)benzylamine

A three neck flask (500 ml) was charged with N,N-diethylchlorometatoluylamidium chloride (25 g, 0.1 mol) which was synthesized above, a spray-dried potassium fluoride (Morita Chemical Co., Ltd., 23.5 g, 0.4 mol) and acetonitrile (250 g), and they were reacted at a refluxing temperature of acetonitrile for 18 hours under nitrogen atmosphere. After finishing the reaction, the solution was cooled down to room temperature and filtered to obtain an acetonitrile solution containing a fluorine exchanged product of N,N-diethylchlorometatoluylamidium chloride. This solution was distilled by means of a precision distilling column having a theoretical plate number of 80 plates. N,N-diethyl-α, α-difluoro(3-methyl)benzylamine (hereinafter, this compound shall be abbreviated as DEET-F) 13 g was obtained as a fraction (pressure: 2 mm Hg) distilled at a temperature of 50 to 60° C. The isolation yield by distillation was about 60% based on N,N-diethylchlorometatoluylamidium chloride. The fraction thus obtained was a colorless transparent liquid and had the following properties.

Heat Stability:

The fraction was slowly heated up to 200° C. in a capillary tube (sealed tube) and maintained for one hour. Decomposition was not observed, and it was thermally stable. In thermal analysis carried out by TG-DTA, a slow weight reduction was observed, but generation or absorption of heat and a sudden change in the weight which showed heat decomposition were not found.

Fluorine Content:

Calculated value: 17.8% by weight, measured value: 17.6% by weight.

NMR data:
$^1$H-NMR: δ value (ppm), TMS standard, measured in $CDCl_3$ 1.02 (t, 6H, $-CH_3$×2), 2.33 (s, 3H, $-CH_3$), 12.84 (q, 4H, $-CH_3$×2)

$^{13}$C-NMR: δ value (ppm), TMS standard, measured at −50° C. in $CDCl_3$ 13.7 (s, $-CH_3$×2), 21.2 (s, $-CH_3$), 40.0 (s, $-CH_2-$×2), 123.7, 127.1, 128.0, 130.6, 137.9 (s, aromatic ring: $-CH-$×5), 136.2 (t, 32 Hz, $-CF_2$)

$^{19}$F-NMR: δ value (ppm), $CF_3COOH$ standard, measured at −50° C. in $CDCl_3$ −73.7 (s, $=CF_2$)

EXAMPLE 3

Used were each 0.5 time mole of benzyl alcohol, octyl alcohol, benzaldehyde, epiandrosterone, benzoic acid and methyl hydroxyisobutyrate and an equivalent mole of water based on DEET-F, and they were reacted. The reaction results thereof are shown in Table 1.

TABLE 1

| | Reaction conditions | | | |
|---|---|---|---|---|
| Reactant | Temperature (° C.) | Time (h) | Product | Yield (%) |
| Water | 20 | 0.5 | DEET | 100 |
| Benzyl alcohol | 20 | 18 | Benzyl fluoride | 100 |
| Epiandrosterone | 20 | 6 | Epiandrostene fluoride | 70 |
| Octyl alcohol | 20 | 5 | Octyl fluoride | 70 |
| Benzaldehyde | 80 | 8 | Difluorotoluene | 40 |
| Benzoic acid | 20 | 6 | Benzoyl fluoride | 80 |
| Methyl hydroxyisobutyrate | 20 | 5 | Methyl fluoro-isobutyrate | 80 |

EXAMPLE 4

IF$_5$/3HF-triethylamine molten salt was used to fluorinate DEET to thereby obtain DEET-F as the product at a yield of 80%.

EXAMPLE 5

A polyimide film (Kapton H, 10 μm thickness) was subjected to etching treatment with 5%-NaOH for 15 minutes and then dried at 110° C. for one hour.

This film was dipped in an acetonitrile containing 10 wt % of DEET-F for 3 hours in a dry box and then pulled up, and it was washed with water and dried. The film was subjected to accelerated test in which it was exposed to a UV ray to examine a gloss retention. The above film was excellent in a gloss retention as compared with a non-treated film and improved by twice as compared with the index value.

INDUSTRIAL APPLICABILITY

The fluorine-containing nitrogen group compounds of the present invention represented by Formula (1) are effective for introducing a fluorine atom into a compound having an active group such as an oxygen-containing functional group. They can be used for uses of surface treatment, cleaning and coating by making use of this reactivity. After the fluorination reaction, they are recovered and can be reused as a starting material for producing the above fluorine compound, and they are useful for various fluorination processes.

What is claimed is:

1. The fluorine compound N,N-diethyl-α,α-difluoro(3-methyl)benzylamine represented by Formula (1):

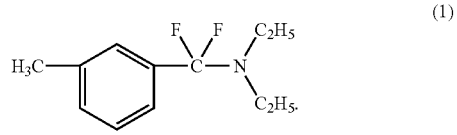

(1)

* * * * *